(12) United States Patent
Carlsson

(10) Patent No.: US 6,358,977 B1
(45) Date of Patent: Mar. 19, 2002

(54) USE OF 4-PIPERIDINEMETHANOL DERIVATIVES IN TREATMENT OF NEURODEVELOPMENTAL DISORDERS

(75) Inventor: Maria Carlsson, Göteborg (SE)

(73) Assignee: A. Carlsson Research AB, Göteborg (SE)

( * ) Notice: Subject to any disclaimer, the term of this patent is extended or adjusted under 35 U.S.C. 154(b) by 0 days.

(21) Appl. No.: 09/674,095

(22) PCT Filed: Apr. 26, 1999

(86) PCT No.: PCT/SE99/00683

§ 371 Date: Dec. 4, 2000

§ 102(e) Date: Dec. 4, 2000

(87) PCT Pub. No.: WO99/56750

PCT Pub. Date: Nov. 11, 1999

(30) Foreign Application Priority Data

Apr. 30, 1998 (SE) ............................................. 9801516

(51) Int. Cl.$^7$ ...................... A61K 31/47; C07D 211/18; C07D 211/22
(52) U.S. Cl. ...................... 514/317; 546/232; 546/241
(58) Field of Search ................................ 546/232, 241; 514/317

(56) References Cited

U.S. PATENT DOCUMENTS 3,992,546 A 11/1976 Heubner ...................... 424/267
5,134,149 A * 7/1992 Carr et al. .................... 546/241

FOREIGN PATENT DOCUMENTS

EP          0208235      1/1987    .................. 514/317
WO         WO95/24194    9/1995    .................. 514/317

* cited by examiner

*Primary Examiner*—Alan L. Rotman
*Assistant Examiner*—Raymond Covington
(74) *Attorney, Agent, or Firm*—Burns, Doane, Swecker & Mathis, L.L.P.

(57) ABSTRACT

Disclosed is the use of a compound with Formula (I) wherein n is 2, 3, or 4, and $R_1$, $R_2$, $R_3$, and $R_4$ are each independently hydrogen, $C_{1-6}$ alkyl, halogen, trifluoromethyl, hydroxy, $C_{1-6}$ alkoxy or amino, or an optical isomer or a pharmaceutically acceptable salt thereof for the production of a pharmaceutical composition for treatment of a neurodevelopmental disorder. Also a method for treatment of neurodevelopmental disorders wherein a therapeutically effective amount of said compound is administered to a patient is disclosed.

12 Claims, 2 Drawing Sheets

USE OF 4-PIPERIDINEMETHANOL DERIVATIVES IN TREATMENT OF NEURODEVELOPMENTAL DISORDERS

This application is a 371 of PCT SE99/00683 Apr. 26, 1999.

FIELD OF THE INVENTION

The present invention relates to the use of 4-piperidinemethanol derivatives for the production of a pharmaceutical composition for treatment of neurodevelopmental disorders. The invention also relates to a method for treatment of such disorders.

BACKGROUND

Neurodevelopmental disorders, such as autism, ADHD (Attention Deficit Hyperactivity Disorder) and DAMP (Deficits in Attention, Motor Control and Perception) are quite common and they lead both to suffering for the patient and to high treatment costs for society.

Childhood autism is a chronic condition leading to a life-long handicap of varying severity. Very few individuals with this diagnosis lead an independent life as adults. Cardinal symptoms of autism are impaired sociability, communication and imagination (Wing's triad). Examples of other symptoms are insistence on sameness, reluctance to switch behavioral program, rigidity, stereotypies, defective habituation and a very meagre behavioral repertoire [Kanner L. (1943) Autistic disturbances of affective contact. Nervous Child 2: 217–250]. Asperger's syndrome [Wing L. (1981) Asperger's syndrome: a clinical account. Psychol Med 11: 115–129] is another autism spectrum disorder characterized by pronounced social impairments but with a higher level of cognitive functioning than in autism. The prevalence of autism is 1 to 2 per 1,000 children, if less severely affected cases are included [Gillberg C. (1993) Autism and related behaviours. J Intellectual Disability Research 37: 343–372; Gillberg C., Coleman M. (1992) The biology of the autistic syndromes. 2nd edition, Clinics in Developmental Medicine no 126. Mac Keith Press, London]. Asperger's syndrome is more common, with a prevalence of about 0.5% [Ehlers S., Gillberg C. (1993) The epidemiology of Asperger's syndrome. A total population study. J Child Psychol Psychiat 34: 1327–1350]. Hitherto, pharmacological interventions aimed at alleviating symptoms of autism have been at most partly successful.

There are striking similarities between symptoms seen in autism and those produced by glutamate antagonists in healthy subjects [Carroll M. E. (1990) PCP and hallucinogens. Adv Alcohol Subst Abuse 9: 167–190; Garey R. E., Weisberg L. A., Heath R. G. (1977) Phencyclidine: An overview. J Psychedelic Drugs 9: 280–285; Gerland G. (1996) En riktig människa. Bokförlaget Cura AB, Stockholm; Grandin T. (1992) An inside view of autism. In Schopler E., Mesibov G. B. (eds) High-functioning Individuals with Autism. Plenum Press, New York, pp 105–126; Grandin T. (1996) My experiences with visual thinking sensory problems and communication difficulties. http://www.autism.org/temple/visual.html; Hansen G., Jensen S. B., Chandresh L., Hilden T. (1988) The psychotropic effect of ketamine. J Psychoactive Drugs 20: 419–425; Kootz J. P., Cohen D. J. (1981) Modulation of sensory intake in autistic children. J Am Acad Child Psychiat 20: 692–701; Krystal J. H., Karper L. P., Seibyl J. P., Freeman G. K., Delaney R., Bremner J. D., Heninger G. R., Bowers M. B., Charney D. S. (1994) Subanesthetic effects of the noncompetitive NMDA antagonist ketamine, in humans: Psychotomimetic, perceptual, cognitive, and neuroendocrine responses. Arch Gen Pshychiatry 51: 199–214; Muir K. W., Lees K. R. (1995) Clinical experience with excitatory amino acid antagonist drugs. Stroke 26: 503–515; Sacks O. (1993/1994) An anthropologist on mars. The New Yorker December 27–January 3: 106–125; Schäfer S. (1996) Stjärnor, linser och äpplen—att leva med autism. Bokförlaget Cura AB, Stockholm; Wing L. (1997) Syndromes of autism and atypical development. In Cohen D. J., Volkmar F. R. (eds) Handbook of Autism and Pervasive Developmental Disorders, 2nd edition. John Wiley & Sons, Inc, New York, pp 148–170]. Examples of such symptoms are: distorted perception of all modalities, defective habituation (manifested i.a. as an obsession with trivial matters), perseverant behavior, defective proprioception/misinterpretation of body position in space, difficulties estimating time/time distortion, concrete thinking, rapid mood fluctuations, anxiety, inappropriate/blunted affect, stereotypies, assaultive behavior, apathy/passivity, social withdrawal, catatonia, and dystonia. These similarities are logical, in view of the neuroanatomical and neuroimaging studies showing aberrations in brain regions that are rich in glutamate neurons, such as medial temporal structures like the amygdala and the hippocampus [see e.g. Bauman M., Kemper T. L. (1985) Histoanatomic observations of the brain in early infantile autism. Neurology 35: 866–874; Bauman M. L. (1991) Microscopic neuroanatomic abnormalities in autism. Pediatrics 87: 791–796; Hoon Jr. A. H., et al. (1992) The mesial-temporal lobe and autism: Case report and review. Develop Med Child Neurol 34: 252–265; Raymond G. V., et al. (1996) Hippocampus in autism: a Golgi analysis. Acta Neuropathol 91: 117–119; Chugani H. T., et al. (1996) Infantile spasms: III. Prognostic implications of bitemporal hypometabolism on positron emission tomography. Ann Neurol 39: 643–649], and cortical areas such as the frontal, prefrontal [see e.g. Minshew N. J. (1991) Indices of neural function in autism: Clinical and biological implications. Pediatrics 87: 774–780; Zilbovicius M., et al. (1995) Delayed maturation of the frontal cortex in childhood autism. Am J Psychiatry 152: 248–252] and parietal cortex [see e.g. Courchesne E., et al. (1993) Parietal lobe abnormalities detected on magnetic resonance images of patients with infantile autism. Am J Roentgenology 160: 387–393], indicating deficient glutamate transmission in autism.

ADHD (Attention Deficit Hyperactivity Disorder) and DAMP (Deficits in Attention, Motor Control and Perception) are neurodevelopmental disorders with prevalence rates of about 5% in a child population. DAMP is the term used in Scandinavia and is virtually synonymous to ADHD but describes, apart from the difficulties with attention, the deficits in motor control and the perceptual aberrations.

ADHD/DAMP is 2–3 times more common in boys than in girls. In half of the ADHD/DAMP cases, the symptoms have disappeared or been greatly reduced by 20 years of age. 20–25% of the children with an ADHD/DAMP diagnosis have developed an antisocial personality disorder with criminality and substance abuse by the time they reach 20 years of age.

It is estimated that about a million children in the US with an ADHD diagnosis are treated with psychostimulants like d-amphetamine and methylphenidate, which improve attention, ability to focus, hyperactivity and impulsivity in about 70%. In Europe, the use of psychostimulants to treat ADHD/DAMP is much less frequent than in the US.

Due to the reluctance in many countries to use psychostimulant, potentially addictive, drugs in children, there is a great need to develop effective and safe drugs to treat ADHD/DAMP.

Brain imaging studies indicate hypofunctioning frontal lobes and defect corticostriatal functioning in ADHD/DAMPtsee Lou H. C., et al. (1984) Focal cerebral hypoperfusion in children with dysphasia and/or in attention deficit disorder. Arch Neurol. 41: 825–829; Lou H. C., et al. (1989) Striatal dysfunction in attention deficit and hyperkinetic disorder. Arch Neurol. 46: 48–52; Zametkin A. J., et al. (1990) Cerebral glucose metabolism in adults with hyperactivity of childhood onset. New Engl J Med 323: 1361–1366; Giedd J. N., et al. (1994) Quantitative morphology of the corpus callosum in attention deficit hyperactivity disorder. Am J Psychiatry 151: 665–9; Casey B. J. et al. (1997) Implication of right frontostriatal circuitry in response inhibition and attention-deficit/hyperactivity disorder. J Am Acad Child Adolesc Psychiatry 36: 374–831. Since corticostriatal neurons are glutamatergic, it is reasonable to assume that glutamatergic transmission is deficient in ADHD/DAMP. Whereas autism probably involves a global deficiency in the brain's glutamate systems, it is likely that ADHD/DAMP involves hypofunctioning glutamate neurons in restricted brain areas, notably in the projections from the frontal lobes to the striatum.

SUMMARY OF THE INVENTION

The object of the present invention is to provide new drugs and new methods for treatment of neurodevelopmental disorders. This object is obtained through the use of 4-piperidinemethanol derivatives.

More specifically, the invention relates to the use of a compound with Formula I:

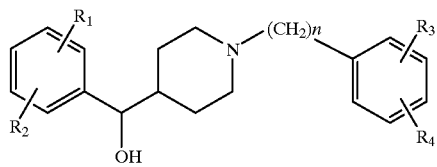

(Formula I)

wherein n is 2, 3, or 4, and $R_1$, $R_2$, $R_3$ and $R_4$ are each independently hydrogen, $C_{1-6}$ alkyl, halogen, trifluoromethyl, hydroxy, $C_{1-6}$ alkoxy or amino, or an optical isomer or a pharmaceutically acceptable salt thereof for the production of a pharmaceutical composition for treatment of a neurodevelopmental disorder.

The invention also relates to a method for treatment of a neurodevelopmental disorder wherein a therapeutically effective amount of a compound with the above given Formula I or an optical isomer or a pharmaceutically acceptable salt thereof is administered to a patient.

DETAILED DESCRIPTION OF THE INVENTION

As stated above, the present invention relates to the use of a compound with Formula I, or an optical isomer or a pharmaceutically acceptable salt thereof for the production of a pharmaceutical composition for treatment of a neurodevelopmental disorder, as well as to a method for treatment of a neurodevelopmental disorder.

The compounds of Formula I may be produced according to any suitable technique known to man skilled in the art. They may e.g. be made by the syntheses described in U.S. Pat. No. 5,169,096 and U.S. Pat. No. 5,134,149, both incorporated herein by reference. A non-limiting example of production of a preferred substance according to the invention, namely (+)-α-(2,3-dimethoxyphenyl)-1-[2-(4-fluorophenylethyl)]-4-piperidine-methanol, described in U.S. Pat. No. 5,134,149, is as follows. An esterification reaction is carried out between racemic α-(2,3-dimethoxyphenyl)-1-[2-(4-fluorophenyl)ethyl]-4-piperidine-methanol and the (+)-isomer of α-methoxyphenylacetic acid, which leads to a diastereomeric mixture. This mixture is subjected to silica gel chromatography which separates the two diastereomers. Thereafter the (+,+)-diastereomer is hydrolyzed to the desired substance.

It is possible to use the compound as a mixture of both enantiomeric forms, but preferably a pure R or S enantiomer is used.

A preferred compound with Formula I for use according to the invention is R-(+)-α-(2,3-dimethoxyphenyl)-1-[2-(4-fluorophenylethyl)]-4-piperidine-methanol (known as M100907).

Examples of neurodevelopmental disorders that can be treated according to the invention are autistic spectrum disorders/autistic continuum disorders, and pervasive developmental disorders (PDDs), such as autism/autistic disorder, childhood/infantile autism, atypical autism, high-functioning autism, Asperger's syndrome, Rett's disorder/syndrome with autistic traits, pervasive developmental disorder not otherwise specified (PDD-NOS), and childhood disintegrative disorder.

There are two major diagnostic systems for pervasive development disorders. One is given in the $4^{th}$ edition of the American Psychiatric Association, Diagnostic and Statistical Manual of Mental Disorders (DSM-IV; 1994) and the other in the $10^{th}$ edition of the World Health Organization, International Classification of Diseases (ICD-10, 1992, 1993), as shown in table 1 below. According to the invention it is possible to treat all these disorders.

TABLE 1

| ICD-10 | DSM-IV |
|---|---|
| Childhood autism | Autistic disorder |
| Atypical autism | Pervasive developmental disorder not otherwise specified (PDD-NOS) |
| Rett's syndrome | Rett disorder |
| Other childhood disintegrative disorder | Childhood disintegrative disorder |
| Overactive disorder with mental retardation with stereotyped movements | No corresponding category |
| Asperger's syndrome | Asperger's disorder |
| Other pervasive developmental disorder | PDD-NOS |
| Pervasive developmental disorder, unspecified | PDD-NOS |

It should be noted that the disease obsessive compulsive disorder (OCD) does not belong to the group pervasive developmental disorders.

Another group of neurodevelopmental disorders that can be treated according to the invention consists of Attention Deficit Hyperactivity Disorder (ADHD), and Deficits in Attention, Motor Control and Perception (DAMP).

The pharmaceutical composition according to the invention may also comprise other substances, such as an inert vehicle, or pharmaceutically acceptable adjuvants, carriers, preservatives etc., which are well known to go persons skilled in the art.

The pharmaceutical composition according to the invention is preferably formulated in a suitable dosage form with a dose size of e.g. 0.1–100 mg.

The term "treatment" used herein relates to both treatment in order to cure or alleviate a disease or a condition, and to treatment in order to prevent an aggravation or the development of a disease or a condition. The treatment may either be performed in an acute, subchronic or in a chronic way.

In the method according to the invention a therapeutically effective amount of a compound with Formula I is administered to a patient. The term "therapeutically effective amount" relates to an amount that will lead to the desired therapeutical effect. The term "patient", as it is used herein, relates to any human or non-human mammal in need of treatment according to the invention.

The pharmaceutical composition and the substance according to the invention may be administered in any suitable way, such as orally in the form of e.g. tablets, capsules, cachets, solutions and emulsions, oromucosally in the form of buccal tablets, rectally e.g. in the form of suppositories transdermally in the form of transdermal patches, or parenterally e.g. in the form of solutions or suspensions for injection or infusion.

The pharmaceutical composition or the substance according to the invention may be administered e.g. as a single daily dose or several times, such as three times, daily.

When the compound used is M100907 (R-(+)-α-(2,3-dimethoxyphenyl)-1-[2-(4-fluorophenylethyl)]-4-piperidine-methanol), a suitable amount is 0.1–100 mg/individual/day when the compound is administered orally, and 0.005–50 mg/individual/day when the compound is administered parenterally.

It is possible to use the pharmaceutical composition and the method according to the invention both in stand alone therapy and as an adjunct to simultaneous psychological and/or alternative pharmacological treatment.

The invention will be further illustrated in the following example, which in no way is intended to limit the scope of the invention.

BRIEF DESCRIPTION OF THE DRAWINGS

In the example below, references are made to the appended drawings on which.

EXAMPLES

The inventor of the present invention and her coworkers have developed an animal model of autism, where mice are rendered hypoglutamatergic by treatment with the glutamate antagonist MK-801 (dizocilpine). Similarly to persons with autism, these hypoglutamatergic animals display defective habituation, perseverant behavior (e.g. relentless forward locomotion, so-called "obstinate progression"), stereotypies, a meager behavioral repertoire and difficulties to change behavioral program. The researchers have chosen to focus their investigation on the defective habituation, since this variable is easily quantified, and a prominent feature of autism.

The defective habituation implies a perception of and a response to the familiar as if it were novel, and can be assumed to underly the phenomenon "insistence of sameness", as well as the extremely high tolerance to monotony, so typical for autism. What is perceived as "same" by most people, is perceived as new by a person with autism.

Animals

Male NMRI mice (B&K Universal AB, Sollentuna, Sweden) weighing 25–30g at the time of testing were used in the experiments. Animals were housed in groups of about 20 per cage for at least one week before the experiment was carried out, with free access to water and food. Temperature: 20–22° C.; 12h light-dark cycle (lights on 6 AM).

Drugs (+)-MK-801 hydrogen maleate (dizocilpine; Research Biochemical Inc) was dissolved in physiological saline. M100907 [(+)-(R)-α-(2,3-dimethoxyphenyl)-1-[2-(4-fluorophenyl) ethyl]-4-piperidinemethanol; courtesy Hoechst Marion Roussel, Inc USA] was dissolved in a few microliters of acetic acid and a 5.5% glucose solution. The injection volume was 10 ml/kg. Control. animals were always given the same solvent as the drug was dissolved in.

Recording of Locomotor Activity

Locomotor activity was measured using activity meters (Diaiscan animal activity monitor, model RXYZM (16) Tao, Omnitech Electronics, Columbus, Ohio, USA). The equipment consists of eight light and sound attenuated boxes (42×42×30 cm) with infrared photo sensors along the front and the side near the floor of the boxes.

Figure 1:
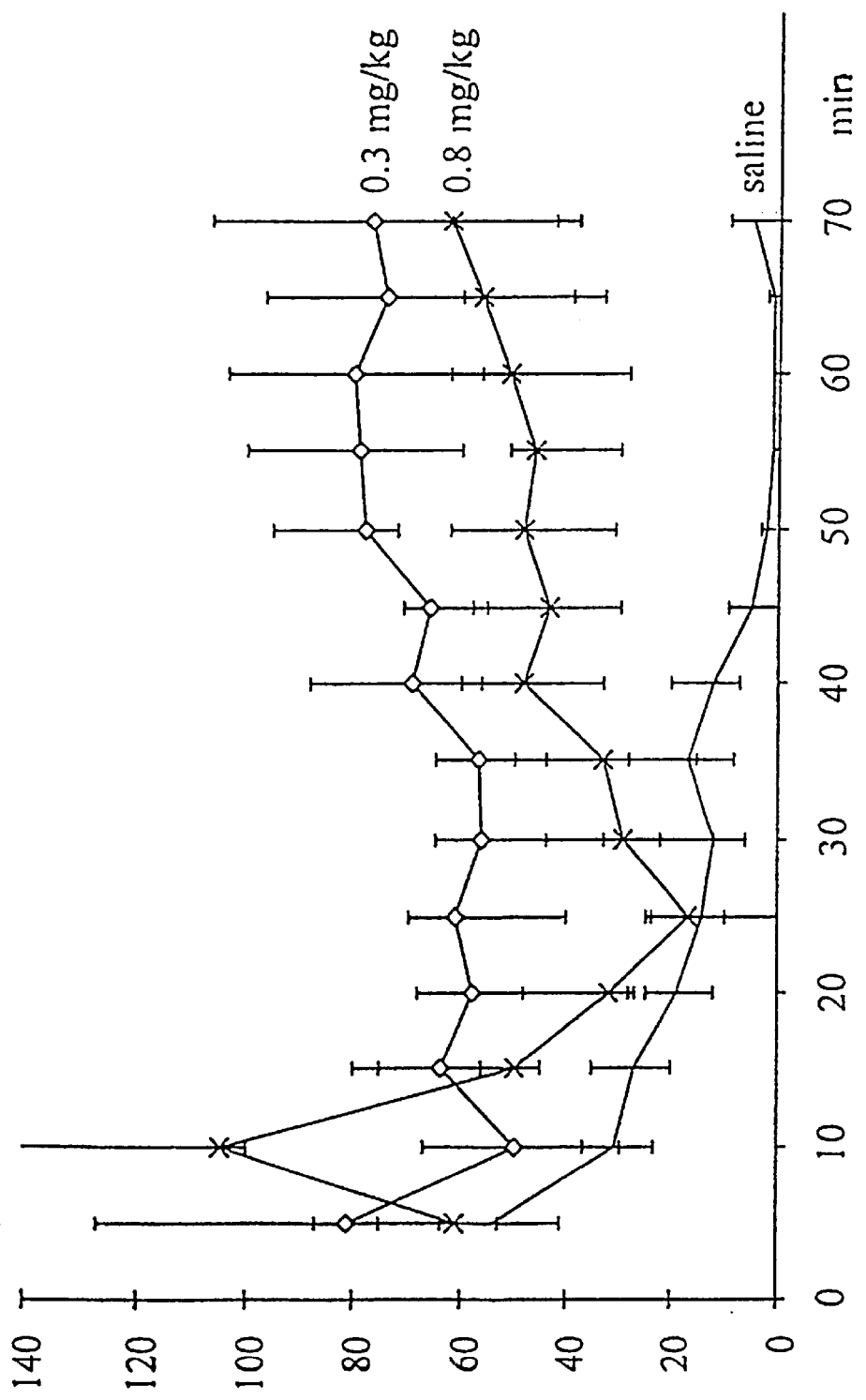
FIG. 1 shows that hypoglutamatergia results in deficient habituation. MK-801 was given intraperitoneally in the dose 0.3 mg/kg or 0.8 mg/kg immediately before the commencement of the behavioral recording, which lasted 70 minutes. The loss of habituation is shown on the ordinate (Y-axis) as counts/5 min interval.

When moved to a novel environment, normal mice display an initial phase of exploratory activity lasting about 30 minutes. Thereafter they are habituated to the new surroundings and settle down, displaying a low activity level FIG. 1 shows the impaired habituation ensuing treatment with 0.3 or 0.8 mg/kg of the glutamate antagonist MK-801. The results shown in the figure are medians and upper and lower quartiles.

A large number of compounds have been tested in this autism model but none of them has been able to affect the MK-801-induced defective habituation without severely interfering with normal behavior. For a long time it seemed impossible to find a compound displaying a specific effect on the autistic-like behavior; the interference with normal behavior was ominous, since it predicted side effects in the clinic.

Figure 2:
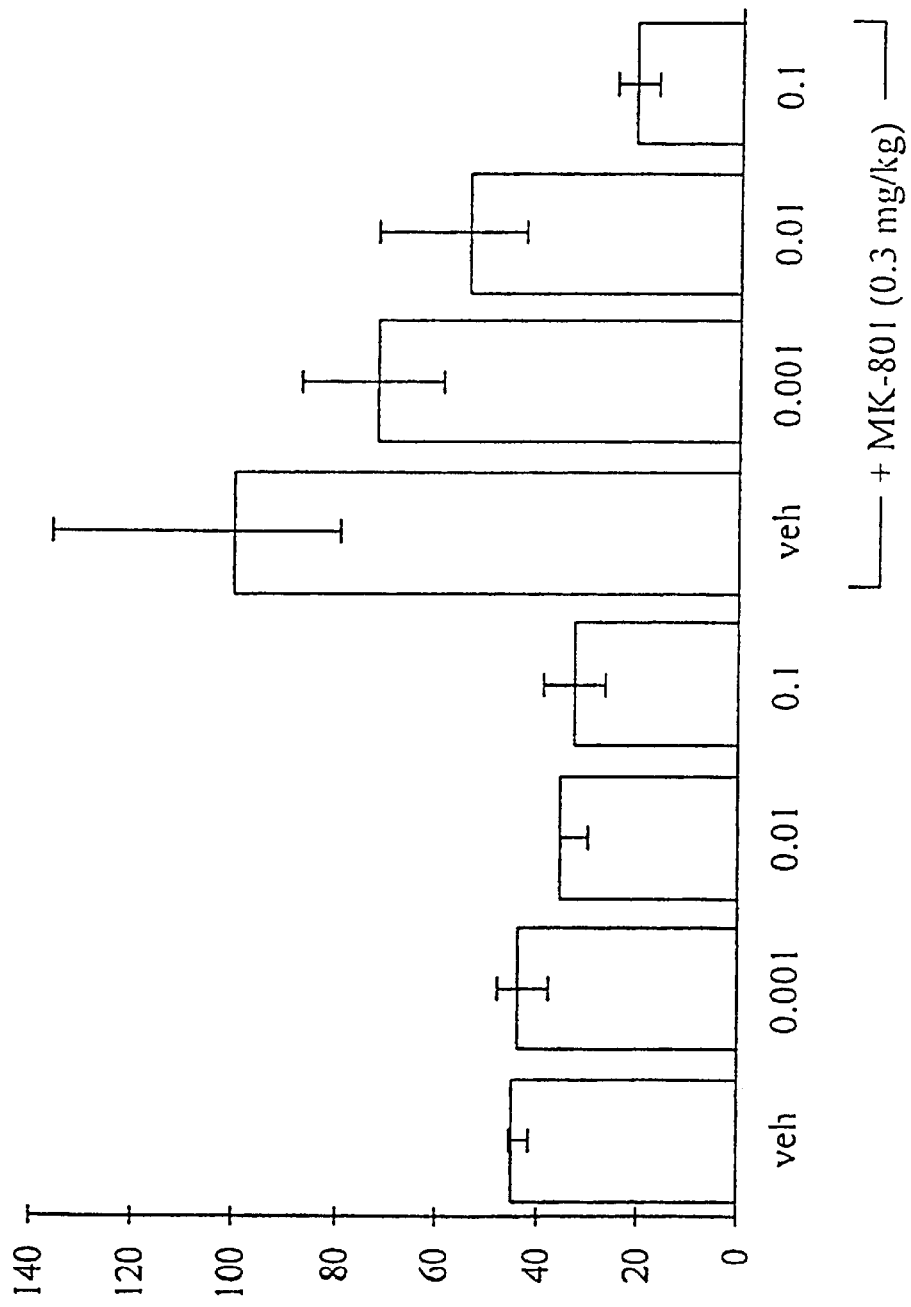
FIG. 2 illustrates that M100907 administered intraperitoneally in doses of 0.001, 0.01 and 0.1 mg/kg, respectively, immediately before the commencement of the behavioral recording, displays anti-autistic effects (veh=vehicle= controls) . The loss of habituation is shown on the ordinate (Y-axis) as m/30 min.

The inventor and her co-workers then tested a compound according to the invention, namely M100907. To their surprise, they found that this compound alleviates the deficient habituation without interfering with normal behavior. These data, illustrating the anti-autistic effects of the compounds according to the invention, are shown in FIG. 2. M100907 was administered intraperitoneally immediately before the commencement of the behavioral recording. The M100907 doses were 0.001., 0.01 and 0.1 mg/kg, respectively. The results shown are medians and upper and lower quartiles (veh=vehicle=controls).

In the example above the mouse data illustrate the efficacy of M100907 in reducing the hyperactivity induced by the glutamate antagonist MK-801. As stated above, it is reasonable to assume that glutamatergic transmission is deficient also in ADHD/DAMP. Whereas autism probably involves a global deficiency in the brain's glutamate systems, it is likely that ADHD/DAMP involves hypofunctioning glutamate neurons in restricted brain areas, notably in the projections from the frontal lobes to the striatum. Reinforcing this is the fact that aberrant perception is a prominent feature in both glutamate antagonist-treated healthy subjects and in ADHD/DAMP-subjects.

In view of this, the compounds according to the invention, such as M100907, should be effective not only in autism, but also in ADHD/DAMP.

What is claimed is:

1. A method for treatment of a neurodevelopmental disorder selected from the group consisting of autistic spectrum disorders/autistic continuum disorders, pervasive developmental disorders (PDDs), Attention Deficit Hyperactivity Disorder (ADHD), and Deficits in Attention, Motor Control and Perception (DAMP), wherein a therapeutically effective amount of a compound with Formula I:

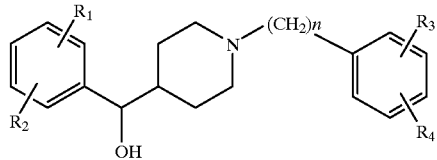

(Formula I)

wherein n is 2, 3, or 4, and $R_1$, $R_2$, $R_3$ and $R_4$ are each independently hydrogen, $C_{1-6}$ alkyl, halogen, trifluoromethyl, hydroxy, $C_{1-6}$ alkoxy or amino, or an optical isomer or a pharmaceutically acceptable salt thereof is administered to a patient in need thereof.

2. A method according to claim 1, wherein said neurodevelopmental disorder is Rett's disorder/syndrome with autistic traits.

3. A method according to claim 1, wherein said neurodevelopmental disorder is pervasive developmental disorder not otherwise specified (PDD-NOS).

4. A method according to claim 1, wherein said neurodevelopmental disorder is childhood disintegrative disorder.

5. A method according to claim 1, wherein said neurodevelopmental disorder is atypical autism.

6. A method according to claim 1, wherein said neurodevelopmental disorder is Asperger's syndrome.

7. A method according to claim 1, wherein said neurodevelopmental disorder is high functioning autism.

8. A method according to claim 1, wherein said neurodevelopmental disorder is autism/autistic disorder.

9. A method according to claim 1, wherein said neurodevelopmental disorder is childhood/infantile autism.

10. A method according to claim 1, wherein said compound with Formula I is used in the form of pure R or S enantiomer.

11. A method according to claim 10, wherein said compound with Formula I is R-(+)-α-(2,3-dimethoxyphenyl)-1-[2-(4-fluorophenylethyl)]-4-piperidine-methanol (M100907).

12. A method according to claim 11, wherein said compound is administered to the patient in an amount of 0.1–100 mg/individual/day orally, or 0.005–50 mg/individual/day parenterally.

* * * * *